US010953888B2

(12) United States Patent
Wilson et al.

(10) Patent No.: US 10,953,888 B2
(45) Date of Patent: *Mar. 23, 2021

(54) AUTONOMOUS VEHICLE MONITORING

(71) Applicant: INTERNATIONAL BUSINESS MACHINES CORPORATION, Armonk, NY (US)

(72) Inventors: John D. Wilson, Houston, TX (US); Kelley Anders, East New Market, MD (US); Jeremy R. Fox, Georgetown, TX (US); Cesar Augusto Rodriguez Bravo, Heredia (CR)

(73) Assignee: International Business Machines Corporation, Armonk, NY (US)

( * ) Notice: Subject to any disclaimer, the term of this patent is extended or adjusted under 35 U.S.C. 154(b) by 86 days.

This patent is subject to a terminal disclaimer.

(21) Appl. No.: 16/182,012

(22) Filed: Nov. 6, 2018

(65) Prior Publication Data

US 2019/0359220 A1    Nov. 28, 2019

Related U.S. Application Data

(63) Continuation-in-part of application No. 15/986,116, filed on May 22, 2018.

(51) Int. Cl.
*G01C 22/00* (2006.01)
*G05D 1/00* (2006.01)
(Continued)

(52) U.S. Cl.
CPC ......... *B60W 40/08* (2013.01); *A61B 5/02055* (2013.01); *A61B 5/18* (2013.01);
(Continued)

(58) Field of Classification Search
CPC ...... B60W 40/08; A61B 5/02055; A61B 5/18; A61B 5/6805; A61B 5/6893; A61B 5/746; A61B 5/747; G05D 1/0055; G05D 1/0088
(Continued)

(56) References Cited

U.S. PATENT DOCUMENTS 6,927,694 B1    8/2005  Smith
7,254,439 B2    8/2007  Misczynski
(Continued)

FOREIGN PATENT DOCUMENTS

CN    102227612 A    10/2011
DE    112012004767 T5    11/2014
(Continued)

OTHER PUBLICATIONS

"Autonomous Vehicle Biometric Medical Emergency Index", an IP.com Prior Art Database Technical Disclosure, Disclosed Anonymously, IP.com No. IPCOM000252775D, IP.com Electronic Publication Date: Feb. 8, 2018, 4 pages, Evidence of Grace Period Use or Sale.
(Continued)

*Primary Examiner* — Mahmoud S Ismail
(74) *Attorney, Agent, or Firm* — Schmeiser, Olsen & Watts; Nicholas L. Cadmus

(57) ABSTRACT

The present invention provides a method and system for monitoring vehicle occupant safety. Biometric conditions of an occupant within an autonomous vehicle currently in motion are monitored via a plurality of sensors. The biometric conditions are analyzed with respect to predetermined baseline biometric conditions associated with the occupant and a medical emergency situation associated with occupant within the autonomous vehicle currently in motion is determined. In response, predetermined actions associated
(Continued)

with resolving the emergency medical situation are executed and a resulting notification indicating the medical emergency situation is transmitted to a predetermined entity.

20 Claims, 9 Drawing Sheets

(51) Int. Cl.
*B60W 40/08* (2012.01)
*A61B 5/00* (2006.01)
*A61B 5/0205* (2006.01)
*A61B 5/18* (2006.01)
*A61B 5/01* (2006.01)
*A61B 5/024* (2006.01)
*A61B 5/021* (2006.01)
*A61B 5/11* (2006.01)

(52) U.S. Cl.
CPC .......... *A61B 5/6802* (2013.01); *A61B 5/6893* (2013.01); *A61B 5/746* (2013.01); *A61B 5/747* (2013.01); *G05D 1/0055* (2013.01); *G05D 1/0088* (2013.01); *A61B 5/0077* (2013.01); *A61B 5/015* (2013.01); *A61B 5/021* (2013.01); *A61B 5/024* (2013.01); *A61B 5/1112* (2013.01); *A61B 2562/0257* (2013.01); *B60W 2040/0818* (2013.01)

(58) Field of Classification Search
USPC .......................................................... 701/23
See application file for complete search history.

(56) References Cited

U.S. PATENT DOCUMENTS

| | | | |
|---|---|---|---|
| 7,427,924 B2 | 9/2008 | Ferrone | |
| 7,979,173 B2 | 7/2011 | Breed | |
| 8,725,311 B1 | 5/2014 | Breed | |
| 9,142,127 B1 | 9/2015 | McDevitt-Pimbley | |
| 9,599,986 B1* | 3/2017 | Eberbach | B60K 28/06 |
| 9,747,793 B1 | 8/2017 | Li | |
| 10,007,263 B1 | 6/2018 | Fields | |
| 2006/0200008 A1 | 9/2006 | Moore-Ede | |
| 2010/0100510 A1 | 4/2010 | Balaban | |
| 2014/0135598 A1 | 5/2014 | Weidl | |
| 2014/0309806 A1 | 10/2014 | Ricci | |
| 2015/0066284 A1 | 3/2015 | Yopp | |
| 2015/0149023 A1 | 5/2015 | Attard | |
| 2016/0071418 A1 | 3/2016 | Oshida | |
| 2016/0140299 A1 | 5/2016 | Al Harbi | |
| 2016/0303969 A1* | 10/2016 | Akula | A61B 5/0022 |
| 2017/0101054 A1* | 4/2017 | Dusane | G08G 1/205 |
| 2017/0105104 A1 | 4/2017 | Ulmansky | |
| 2017/0108342 A1 | 4/2017 | Foreman | |
| 2017/0151959 A1 | 6/2017 | Boesen | |
| 2018/0120837 A1 | 5/2018 | Regmi | |
| 2018/0308064 A1 | 10/2018 | Glaser | |
| 2018/0338241 A1 | 11/2018 | Li | |
| 2018/0375939 A1 | 12/2018 | Magalhães De Matos | |
| 2018/0376305 A1 | 12/2018 | Ramalho De Oliveira | |
| 2018/0376306 A1 | 12/2018 | Ramalho De Oliveira | |

FOREIGN PATENT DOCUMENTS

| | | |
|---|---|---|
| JP | 2015133050 A | 7/2015 |
| WO | 2017018842 A1 | 2/2017 |
| WO | 2017018852 A1 | 2/2017 |

OTHER PUBLICATIONS

"OnStar", Wikipedia, this page was last edited on Feb. 28, 2018, 7 pages, <https://en.wikipedia.org/wiki/OnStar>.
"Seizure While Driving", Epilepsy Foundation, last printed Mar. 13, 2018, 25 pages, <https://www.epilepsy.com/connect/forums/living-epilepsy-adults/seizure-while-driving-1>.
Burchell, Bill; Etihad Introduces Onboard Passenger Health Monitoring; Feb. 25, 2010; http://aviationweek.com/awin/etihad-introduces-onboard-passenger-health-monitoring; 2 pages.
D'Allegro, Joe; Soon your car will know when you are having a heart attack—and know how to react; CNBC.com; Nov. 17, 2017; https://www.cnbc.com/2017/11/17/cars-will-know-when-youre-having-a-heart-attack-and-how-to-react.html; 6 pages.
De Lille, Christing; Flightbeat; https://www.tudelft.nl/en/ide/research/research-labs/aviation/education/flightbeat/; retrieved from the Internet Nov. 6, 2018; 3 pages.
Friedman, Mark; List of IBM Patents or Patent Applications Treated as Related; Nov. 6, 2018; 1 page.
Kavitha, K.C. et al.; Smart wireless healthcare monitoring for drivers community; 2014 International Conference on Communication and Signal Processing; Apr. 3-5, 2014; 2 pages.
Mell et al., "The NIST Definition of Cloud Computing", National Institute of Standards and Technology, Special Publication 800-145, Sep. 2011, 7 pages.
Patil, Savita; In-Vehicle Driver Health Monitoring System; International Journal of Technology and Science, ISSN (Online 2350-1111, (Print) 2350-1103; vol. 9, Issue 2; 2016; pp. 38-40.
Prigg, Mark; Engineers develop a car that can monitor your Health as you drive—and take over if you become ill or fall asleep; Jul. 11, 2013; http://www.dailymail.co.uk/sciencetech/article-2360694/Ford-car-monitor-Health-drive--ill-fall-asleep.html; 4 pages.
Safe Car News; Ford combines driver health monitoring and ADAS; Jan. 12, 2016; http://safecarnews.com/ford-combines-driver-health-monitoring-and-adas_ja7126/; 6 pages.
Strickland, Eliza; 3 Ways Ford Cars Could Monitor Your Health; IEEE Spectrum; May 19, 2017; https://spectrum.ieee.org/the-human-os/biomedical/diagnostics/3-ways-ford-cars-could-monitor-your-health; 7 pages.
Tata Elxsi; In-car health and wellness monitoring; http://www.tataelxsi.com/Perspectives/WhitePapers/In%20car%20wellness.pdf; retrieved from the Internet Nov. 6, 2018; 10 pages.
Van Wagenen, Juliet, "The Next Generation of Ambulance Technology Hits the Road", HealthTech, Copyright © 2018 CDW LLC, 5 pages, <https://healthtechmagazine.net/article/2017/04/next-generation-ambulance-technology-hits-road>.

* cited by examiner

US 10,953,888 B2

AUTONOMOUS VEHICLE MONITORING

CROSS REFERENCE TO RELATED APPLICATIONS

This application is a continuation-in-part application claiming priority to Ser. No. 15/986,116 filed May 22, 2018, the contents of which are hereby incorporated by reference.

FIELD

The invention relates generally to getting help in an emergency medical situation for an occupant in an autonomous vehicle, and in particular to a method and system for coordinating a meeting of the autonomous automotive vehicle with an ambulance or other emergency service vehicle manned by emergency service personnel.

BACKGROUND

When a person traveling in an autonomous automotive vehicle, i.e. a driverless vehicle, requires emergency medical attention it sometimes takes a long time for specified help to reach the autonomous automotive vehicle and the person in need. For example, minutes and seconds can be critical in saving the person's life such that a system may quickly bring together the autonomous automotive vehicle with specified help.

SUMMARY

The present invention provides a vehicle occupant safety monitoring method comprising: monitoring via a plurality of sensors, by a processor of a hardware device within an autonomous vehicle in motion, biometric conditions of an occupant within the autonomous vehicle currently in motion; analyzing, by the processor, the biometric conditions with respect to predetermined baseline biometric conditions associated with the occupant; determining, by the processor based on results of the analyzing, a medical emergency situation associated with the occupant within the autonomous vehicle currently in motion; executing, by the processor, a plurality of predetermined actions associated with resolving the emergency medical situation; and transmitting, by the processor to a predetermined entity, a notification indicating the a medical emergency situation and results of the executing.

The present invention provides a computer program product, comprising a computer readable hardware storage device storing a computer readable program code, the computer readable program code comprising an algorithm that when executed by a computer processor of a hardware device within an autonomous vehicle in motion implements a vehicle occupant safety monitoring method, the method comprising: monitoring via a plurality of sensors, by the processor, biometric conditions of an occupant within the autonomous vehicle currently in motion; analyzing, by the processor, the biometric conditions with respect to predetermined baseline biometric conditions associated with the occupant; determining, by the processor based on results of the analyzing, a medical emergency situation associated with the occupant within the autonomous vehicle currently in motion; executing, by the processor, a plurality of predetermined actions associated with resolving the emergency medical situation; and transmitting, by the processor to a predetermined entity, a notification indicating the medical emergency situation and results of the executing.

The present invention provides a hardware device, within an autonomous vehicle in motion, comprising a computer processor coupled to a computer-readable memory unit, the memory unit comprising instructions that when executed by the computer processor implements a vehicle occupant safety monitoring method comprising: monitoring via a plurality of sensors, by the processor, biometric conditions of an occupant within the autonomous vehicle currently in motion; analyzing, by the processor, the biometric conditions with respect to predetermined baseline biometric conditions associated with the occupant; determining, by the processor based on results of the analyzing, a medical emergency situation associated with the occupant within the autonomous vehicle currently in motion; executing, by the processor, a plurality of predetermined actions associated with resolving the emergency medical situation; and transmitting, by the processor to a predetermined entity, a notification indicating the medical emergency situation and results of the executing.

Embodiments of the present invention advantageously provides a simple method and associated system capable of accurately detecting user activities.

DETAILED DESCRIPTION

Figure 1:
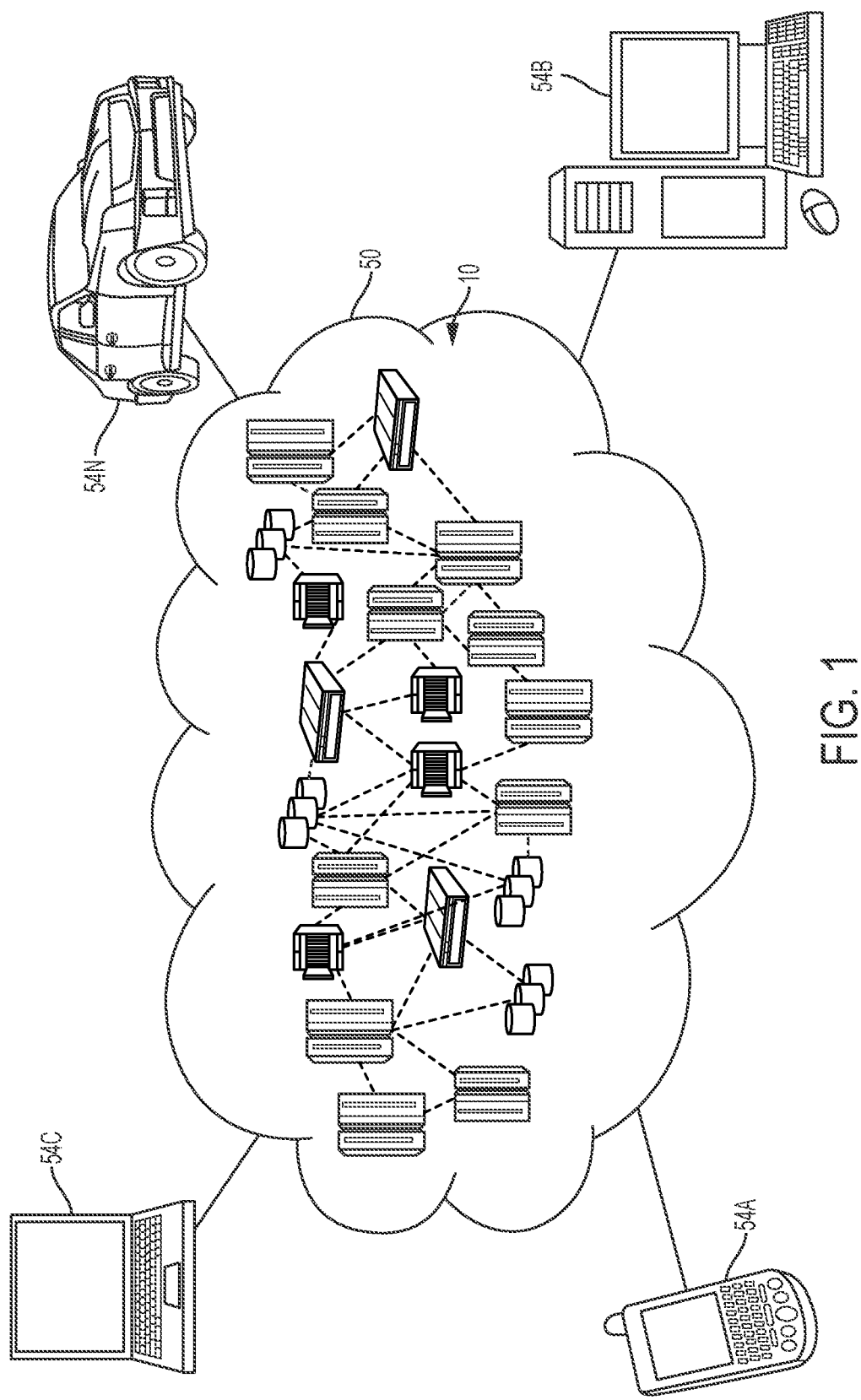
FIG. 1 depicts a cloud computing environment according to an embodiment of the present invention.

In the following description, specific details are set forth although it should be appreciated by one of ordinary skill that the present invention can be practiced without at least some of the details. In some instances, known features or processes are not described in detail so as not to obscure the present invention.

An autonomous car, also known as an autonomous automotive vehicle, a driverless car, self-driving car, or robotic car, is an automotive vehicle that is capable of sensing its environment and navigating without human input. An autonomous automotive vehicle detects surroundings using radar, lidar, GPS, odometry, and computer vision. Advanced control systems interpret sensory information to identify appropriate navigation paths, as well as obstacles and relevant signage.

Autonomous automotive vehicles are currently being tested to chauffeur human passengers. In the event that an emergency medical situation is detected regarding a passenger who is riding in an autonomous automotive vehicle, time may be critical to get medical help for the passenger. The autonomous automotive vehicle could change its route and destination to head to the nearest hospital having emergency services. Alternatively, the autonomous automotive vehicle could stop, park and summons an ambulance by making a 911 emergency phone call. However sometimes neither of the two previously mentioned approaches would yield the quickest response time for emergency medical personnel to reach the autonomous automotive vehicle and the passenger in need of help.

According to the systems and methods of the present invention, a quickest simultaneous arrival time at a safe rendezvous location is determined for the autonomous automotive vehicle to meet an ambulance after notification of a passenger of the autonomous automotive vehicle requiring emergency medical assistance. The inventive methods can be implemented via a computer system, e.g. an on-board vehicle rendezvous coordination system built into the autonomous automotive vehicle and which could use a GPS global positioning system and wireless cloud technology for communications with an (EMS) Emergency Medical Service, e.g. an ambulance service.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
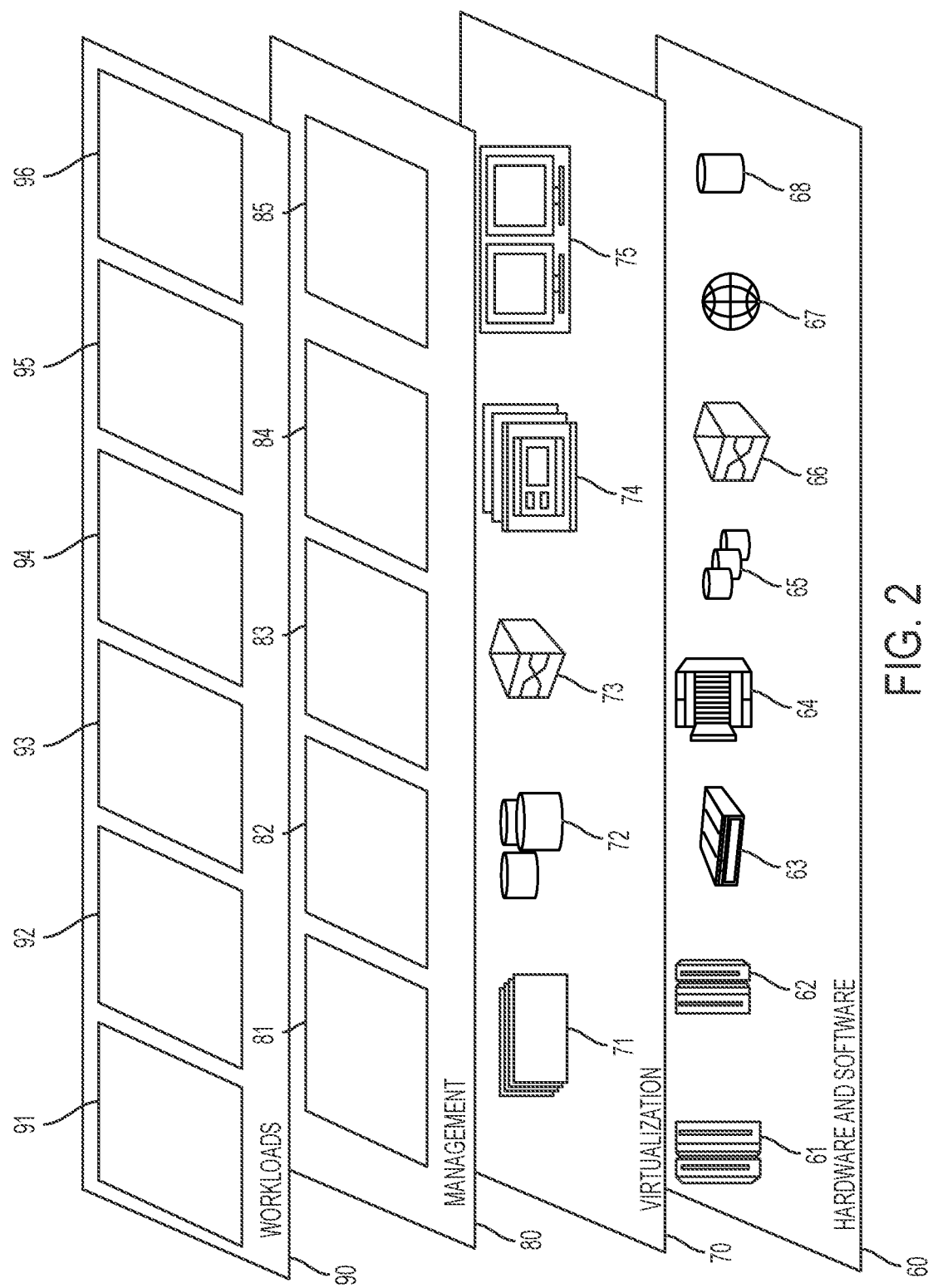
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and improving automotive technology by monitoring vehicle occupant safety and generating associated actions 96.

Figure 3A:
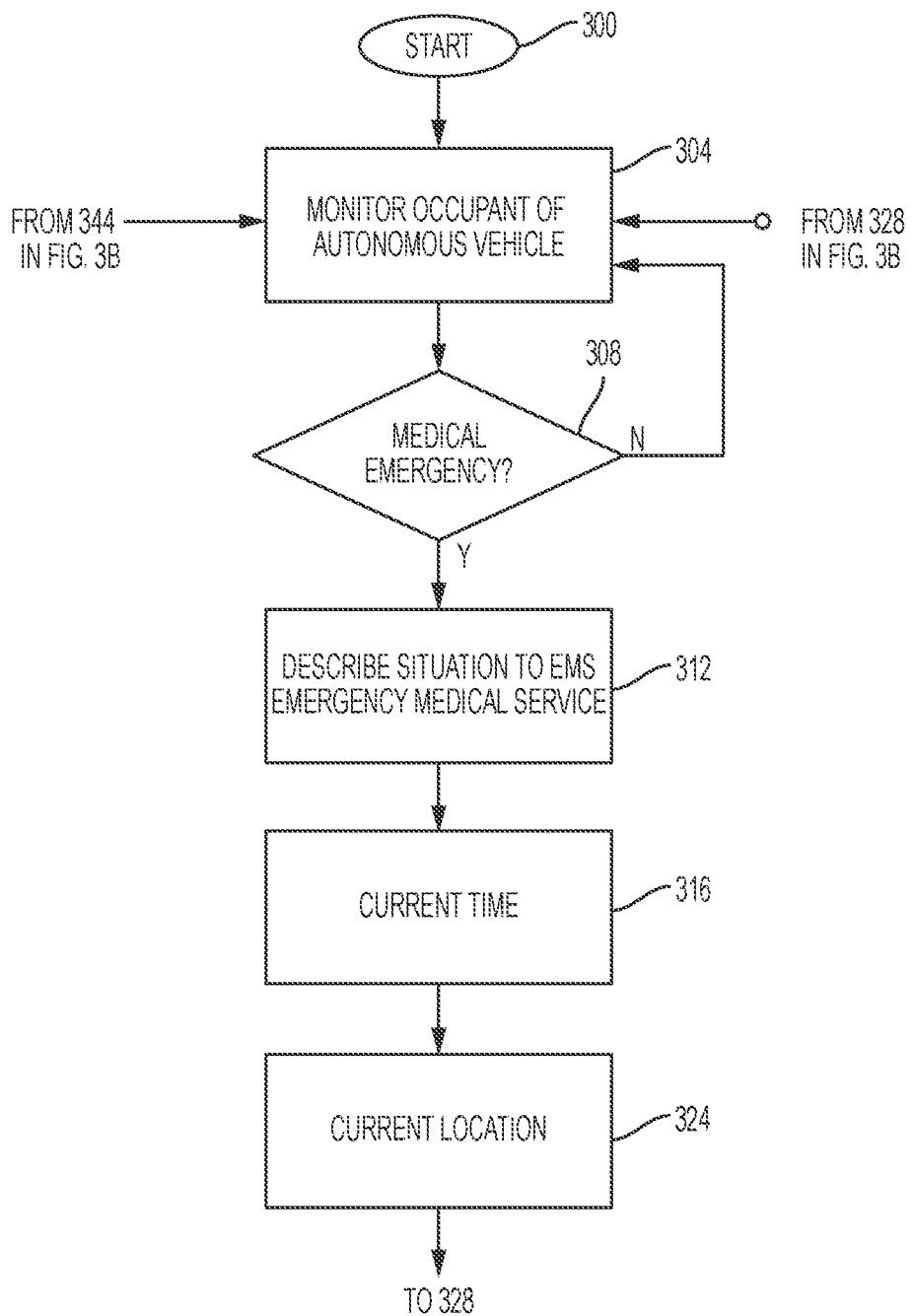
FIGS. 3A and 3B together provide a flow chart diagram of a method in accordance with embodiments of the present invention.
Figure 3B:
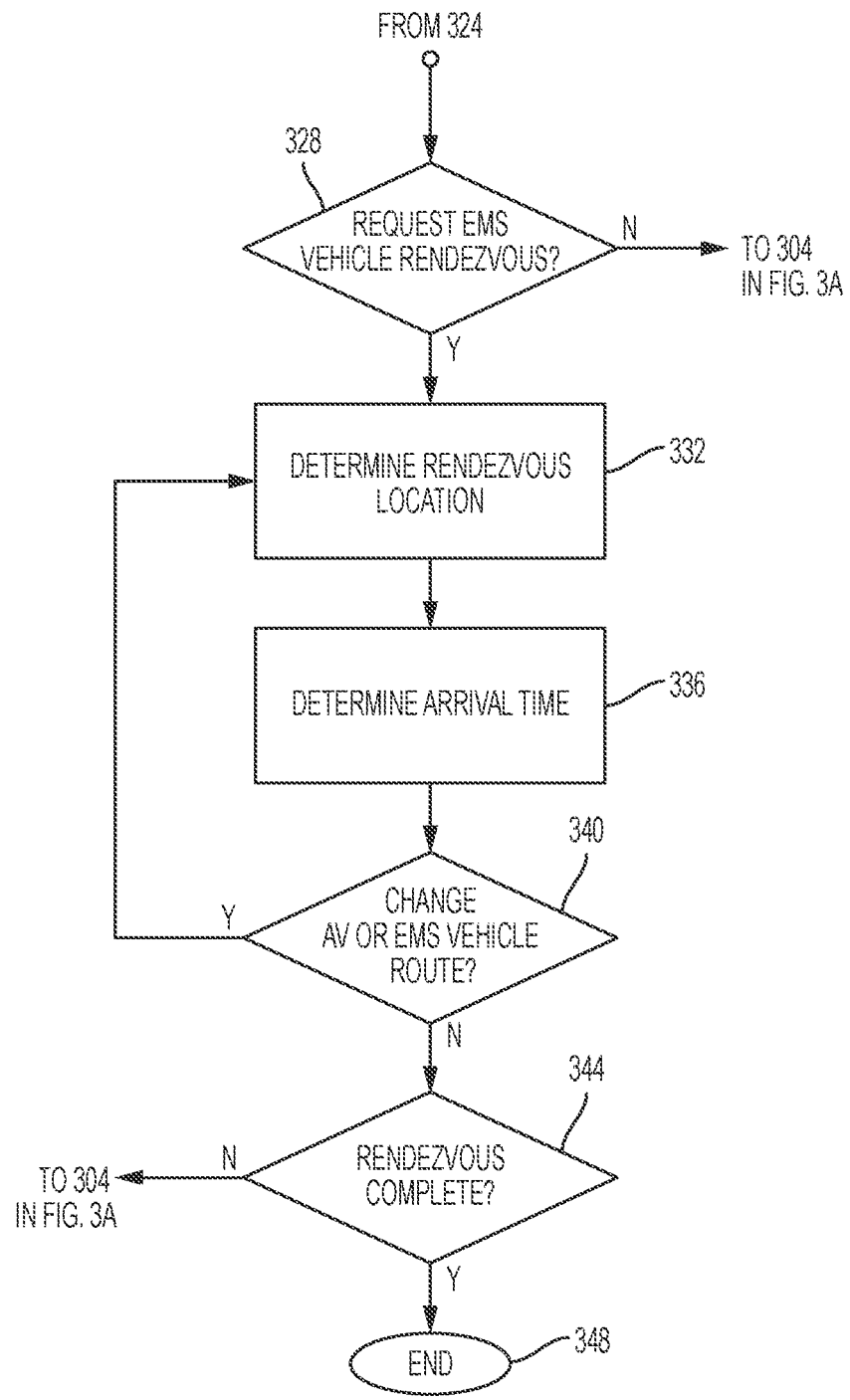

FIGS. 3A and 3B together provide a flow chart diagram of a method in accordance with embodiments of the present invention.

The vehicle rendezvous coordination method starts in step 300 of FIG. 3A. It is implemented by a computer system within the autonomous automotive vehicle which includes wireless communications capabilities. The method can be set up to start (i) when the autonomous automotive vehicle is started, e.g. upon ignition of the vehicle motor, (ii) when a passenger first enters the vehicle, or (iii) when the vehicle starts moving towards its destination with the passenger on-board. In the first case the vehicle rendezvous coordination method is running at all times whenever the vehicle is operational. In the second case, the vehicle rendezvous coordination method is only activated when a passenger is detected within the vehicle, and in the third case the method only operates when the vehicle is driving towards a destination with a passenger on-board.

The health status of all passengers is monitored in step 304 as described for instance in the related patent application entitled "System and Method for UAV Enabled Medical Assistance" filed at the USPTO on the same date herewith by John D. Wilson et al. and hereby incorporated by reference in its entirety for background information only.

The method in step 300 first detects that a passenger is present within the autonomous automotive vehicle. Thereafter the behavior and well-being of the passenger, i.e. occupant, in the vehicle is continuously monitored using sensors within the vehicle. For example, audio sounds can be detected from a microphone whereby verbalizations of the passenger are digitally signal processed to search for matching sounds which would indicate a medical crisis such as but not limited to: choking; gasping for air; crying in pain; vomiting; screaming; calling for medical help; groaning; and complete silence indicating lack of breathing.

Various biometric Internet of Things (IoT) sensors within the vehicle can be used to measure the passenger's health status such as but not limited to:

Odor Sensors to detect smell signatures of bodily fluids.

Moisture Sensors to detect moisture occurrence in the seat, on the floor mats, on arm rests, and door handles.

Accelerometers to analyze motion of the passenger with respect to car motion, such as slumping forward or thrusting backwards.

Directional Thermometers to detect changes in the passenger's body temperature, such as a high or low body temperature indicating a possible health emergency.

Cameras within the autonomous automotive vehicle can also be used to improve the awareness of medical issues of the passenger. For instance, cameras and associated data analysis software can view and detect changes in the appearance of the passenger such as, but not limited to: swelling of body parts; dilated pupils; facial color changes; sweating; changes over time of the reflectiveness of the passenger's face due to sweating; gestures such as hands to the throat or flailing arms; holding his head; clutching his chest; constantly rubbing his face; and appearing to be collapsed or unconscious.

Step 308 analyzes the data gathering from the monitoring step 304 to determine whether the passenger of the autonomous automotive vehicle is potentially experiencing a medical emergency situation. If no medical emergency is detected, then the process continues back to step 304 for continued monitoring. If a possible medical emergency is detected in step 308 then the method moves to step 312 where an Emergency Medical Service is contacted and alerted of the situation, including being provided with the data gathered from all the sensors that are monitoring the passenger's health. The EMS can be any entity which provides an ambulance or other mobile emergency health care unit with emergency medical personnel in order to stabilize a person having a medical emergency, then transporting that person to a hospital or similar health care facility for follow-up treatment. For the purposes of the current invention, the EMS is defined as any service which can send a mobile unit with emergency medical personnel to a person in need of emergency care and transport. For instance, the EMS can be an ambulance service, a police station, a hospital, fire department, etc. The emergency medical personnel are defined as any persons having training to handle emergency situations such as ambulance attendants, emergency medical technicians (EMT), police, firemen, doctors, nurses, physician assistants, etc. Moreover, the EMS vehicle can be any vehicle, such as but not limited to an ambulance, a car, a truck, a helicopter, an airplane, a police car, an off-road vehicle, a snowmobile, an amphibious vehicle, and a watercraft, which can carry medical emergency personnel and transfer the patient to a medical facility.

In step 312 data detailing the medical condition of the passenger in the autonomous automotive vehicle is communicated to emergency medical services within a predetermined radius (e.g. 20 miles) or predetermined driving distance of the autonomous automotive vehicle. The communications are one-way or two-way communications systems preferably provided by the computer system by way of any known wireless communications device, e.g. communications via a smart phone, mobile computer device, radio, satellite, Internet or other wireless network. Also transmitted to the EMS and stored within the computer system when an emergency is detected is the current time in step 316 and the current location of the autonomous automotive vehicle in step 324. An EMS is selected, typically the closest, which could provide an ambulance to meet the autonomous automotive vehicle in the shortest time possible.

Step 328 in FIG. 3B determines whether an ambulance is needed based upon the totality of data gathered while monitoring the passenger. If a decision is made that an ambulance is not needed, then the method will loop back to step 304 to continue monitoring the passenger. If the medical situation is determined in step 308 to be an emergency that requires trained medical personnel to treat and stabilize the passenger and transport the passenger to a hospital, then an ambulance (or other EMS vehicle) will be dispatched to meet the autonomous automotive vehicle. Typically, an automotive ambulance will be dispatched to aid the passenger in need. However, in some cases the EMS vehicle could be another type of vehicle such as a helicopter to airlift the passenger, or a watercraft vehicle if the nearest hospital is across a lake and the fastest mode of transportation is for a watercraft ambulance vehicle to transport the passenger. Many other EMS vehicles could be used, such as a car, a truck, an airplane, a police car, an off-road vehicle, a snowmobile or an amphibious vehicle.

A rendezvous location is determined in step 332, and an arrival time is determined in step 336 at which the emergency medical vehicle and the autonomous automotive vehicle are estimated to simultaneously arrive at the rendezvous location. Although the arrival times are preferably the same time for both the ambulance and the autonomous automotive vehicle to arrive at the rendezvous location, there will often be an offset of times dues to traffic conditions, weather, etc. In other words, the system may estimate a simultaneous arrival time of 3:37 pm at a selected rendezvous location, but the ambulance could arrive at 3:35 pm and the autonomous automotive vehicle could arrive at 3:38 pm. The simultaneous arrival time is an optimum time which is sought to provide the quickest coordination of medical services to the passenger of the autonomous automotive vehicle.

The rendezvous location is determined, by the computer system, as a safe location which is defined as a location where both the autonomous automotive vehicle and the EMS vehicle can park without blocking traffic to allow expeditious, safe transfer of the occupant from the autonomous automotive vehicle to the EMS vehicle by the EMS personnel. Other safety factors are also considered when determining a safe rendezvous location, such as but not limited to (i) whether the terrain will impede passenger transfer, (ii) whether nearby activities will impede passenger transfer (e.g. a demonstration, parade, sporting event crowd, etc.), (iii) whether the roadway is safe for travel, etc. The safe location can be further defined to exclude (i) areas of statistically high issues, (ii) areas unstable for parking vehicles, (iii) areas unsafe for vehicle ingress or egress, (iv) areas of unsafe air quality, and (v) areas unsafe due to weather or meteorological conditions.

Step 332 determines a list of safe rendezvous locations by examining the current location of the autonomous automotive vehicle and the available EMS services within the nearby area. Estimated travel times are compared for the autonomous automotive vehicle and the EMS vehicle to reach a plurality of different safe locations. One of the plurality of different rendezvous locations is selected which corresponds to having a shortest travel time for both the autonomous automotive vehicle and the ambulance to reach the selected rendezvous location. The estimated travel times are defined as a difference between the current time of the communicated medical emergency situation and the arrival time at each of the respective plurality of different safe locations. The prospective safe rendezvous locations can also be determined by comparing a plurality of different travel routes of the autonomous automotive vehicle and the EMS vehicle to reach the locations, thereafter selecting the rendezvous location which corresponds to having a shortest combined travel distance of the autonomous automotive vehicle and the EMS vehicle to the selected rendezvous location.

Sometimes the status of a selected rendezvous location can change, or the routes to the selected rendezvous location for either the EMS vehicle or the autonomous automotive vehicle can become inaccessible or delayed due to unforeseen circumstances such as an automobile accident blocking the roadway. Step 340 determines whether a change of route is suggested for either the autonomous automotive vehicle or the EMS vehicle. If no change of route is necessary, then the process continues to step 344 and further continues to monitor the passenger in step 304 until the rendezvous is complete. When both the autonomous automotive vehicle and the EMS vehicle have arrived at the selected safe rendezvous location, then the method ends in step 348.

If step 340 determines that a change of route is suggested for either the autonomous automotive vehicle or the EMS vehicle, then the method returns to step 332 to determine whether the same rendezvous location should be maintained or not. If the same rendezvous location is kept, then a further analysis will determine whether the same route should be used or whether a different route should be used for either of the vehicles. It may be that the quickest route to the original rendezvous location is still the same route, albeit delayed due to unforeseen circumstances. Alternatively, a different route may be chosen as the fastest route.

Other safe rendezvous locations will be considered and compared with the original rendezvous location to determine which location could be reached as fast as possible. Any decision for either the autonomous automotive vehicle or the EMS vehicle to use a different route or to travel to a different safe rendezvous location will be communicated to the EMS service as well as being acknowledged by the computing system in the autonomous automotive vehicle. Monitoring of the passenger will continue in step 304 until the rendezvous is completed as determined in step 344 at which time the process ends in step 348.

The vehicle rendezvous coordination system and method can include independent GPS mapping capabilities or it can use a separate on-board GPS system which has been installed in the autonomous automotive vehicle. An automotive GPS system is well known to provide route mapping and travel data for the vehicle in which it is installed.

Figure 3C:
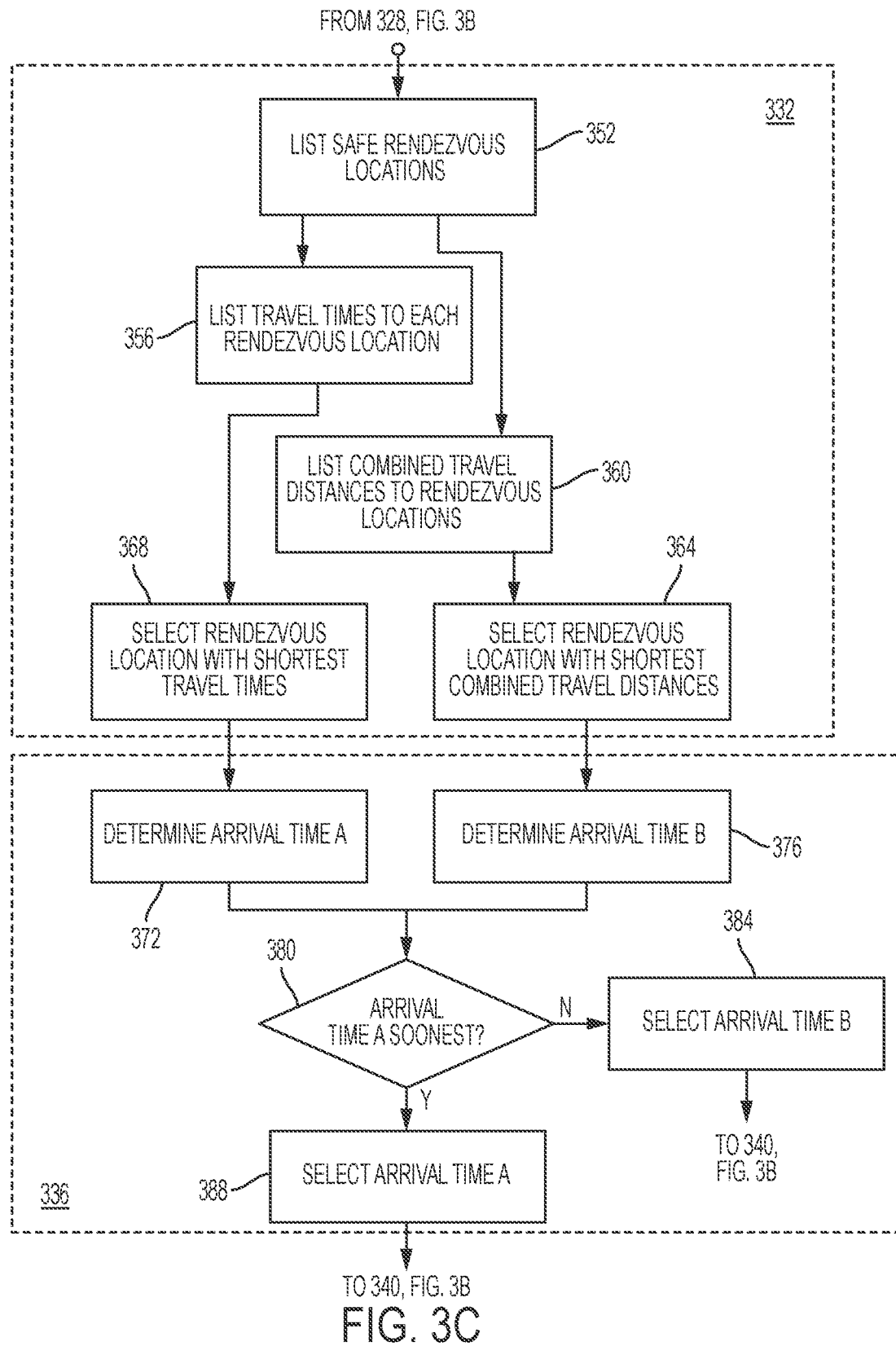
FIG. 3C shows expanded views of select steps of the flow chart of FIG. 3B.

FIG. 3C shows expanded views of steps 332 and 336 of the flow chart of FIG. 3B. Step 332 determines a rendezvous location for the autonomous vehicle to meet the EMS vehicle in the event of a medical emergency of a passenger traveling in the autonomous automotive vehicle and requiring emergency medical treatment followed by transport to a hospital. In step 352 a list of safe rendezvous locations is determined which are easily accessible to both the ambulance and the autonomous automotive vehicle. A coordinating list of travel times is compiled in step 356 for travel to each of the listed safe rendezvous locations for both (i) the ambulance from its current location such as at the EMS service address or elsewhere, and (ii) the autonomous automotive vehicle from its current location. Step 368 analyzes all the listed rendezvous locations and selects an optimum one of the safe rendezvous locations which has the shortest travel times for arrival of the ambulance and the autonomous automotive vehicle. The optimum routes are preferably selected so that both the ambulance and the autonomous automotive vehicle will have the same travel times and will both arrive at the rendezvous location at the same time. However, an optimum safe rendezvous location could be selected which would result in different travel times and arrival times for the EMS vehicle and the autonomous automotive vehicle.

In one example a safe rendezvous location A may have a 12 minute travel time for the ambulance and a 12 minute travel time for the autonomous automotive vehicle totaling 24 minutes combined. A safe rendezvous location B may have a 12 minute travel time for the ambulance and a 10 minute travel time for the autonomous automotive vehicle totaling 22 minutes combined. In either case the passenger will have to wait for 12 minutes before EMS personnel from the ambulance will be able to care for him and begin his transport to the hospital. However it is preferable for the method to select rendezvous location B which has a two minute buffer to offset possible traffic congestion or other delays of the autonomous automotive vehicle while traveling to the rendezvous location.

Step 360 generates a coordinating list of travel distances corresponding to the autonomous automotive vehicle and the EMS vehicle each traveling to the list of safe rendezvous locations compiled in step 356. The travel distances include distances for both (i) the ambulance from its current location such as at the EMS service address or elsewhere to each rendezvous location, and (ii) the autonomous automotive vehicle from its current location to each rendezvous location. Step 364 analyzes all the listed rendezvous locations and travel distances, then selects an optimum one of the safe rendezvous locations which has the shortest combined travel distances for travel by the ambulance and the autonomous automotive vehicle. The optimum routes are preferably selected so that both the ambulance and the autonomous automotive vehicle will arrive at the rendezvous location at the same time. However, an optimum safe rendezvous location could be selected which would result in different travel times and arrival times for the EMS vehicle and the autonomous automotive vehicle.

Arrival times of the ambulance and the autonomous automotive vehicle at the safe rendezvous locations are determined in step 336. In FIG. 3C step 372 determines the arrival time A of the ambulance and the autonomous automotive vehicle at the safe rendezvous location selected in step 368 as having the shortest travel times. Step 376 determines the arrival time B of the ambulance and the autonomous automotive vehicle at the safe rendezvous location selected in step 364 as having the shortest combined travel distances. Then decision step 380 decides which arrival time is sooner, arrival time A or arrival time B. If arrival time A is sooner, then the method selects arrival time A in step 388 and continues to step 340 of FIG. 3B. If arrival time B is sooner, then the method selects arrival time B in step 384 and continues to step 340.

Figure 4:
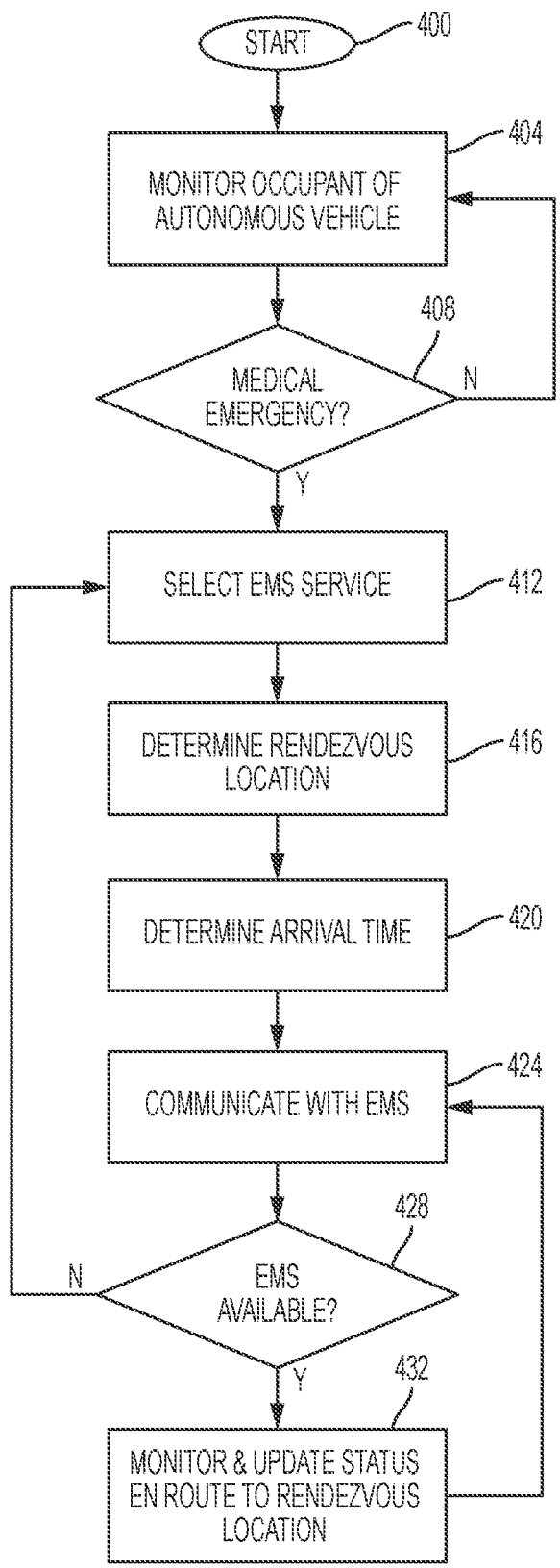
FIG. 4 is a flow chart diagram of a method in accordance with additional embodiments of the present invention.

FIG. 4 is a flow chart diagram of a method in accordance with additional embodiments of the present invention. The method starts in step 400 when a passenger enters the autonomous automotive vehicle. As long as the passenger is an occupant of the vehicle his medical health will be monitored in step 404 as previously discussed. If a potential emergency medical situation is detected in step 408 by the various sensors within the autonomous automotive vehicle, then an EMS service is selected in step 412 (at the time of emergency detection) which is located within a predetermined driving distance from the current location of the autonomous automotive vehicle. Alternatively, the EMS could be selected as the closest EMS service to the autonomous automotive vehicle, regardless of its location (e.g. even if its 100 miles away). Otherwise monitoring of the passenger's health continues in step 404. Typically, the closest EMS service would be selected, although other factors such as the availability of specific emergency medical services (an operating room, etc.) can be considered prior to selecting a specific EMS service.

The method continues in step 416 by determining a safe rendezvous location for the autonomous automotive vehicle and an ambulance or other EMS vehicle to meet. The arrival times of the EMS vehicle at the rendezvous location and the autonomous automotive vehicle at the rendezvous location are estimated in step 420. Ideally the two vehicles would meet at exactly the same arrival time at the rendezvous location in order to minimize delay of medical treatment to the passenger, and to minimize delay in getting the passenger into the ambulance for emergency transport to a hospital. This is also the reason why in a preferred embodiment the autonomous automotive vehicle continues to travel (rather than parking in a stationary location) to meet the ambulance at a halfway point from their original positions in order to minimize delay of medical treatment and emergency transport.

In step 424 wireless communications is initiated between the autonomous automotive vehicle and the selected EMS service. The computing system communicates with the EMS service by sending:

(i) a request for an EMS vehicle manned by EMS personnel to be dispatched to the rendezvous location,
(ii) the identified medical emergency situation of the occupant of the autonomous automotive vehicle,
(iii) the current location of the autonomous automotive vehicle,
(iv) the rendezvous location, and
(v) the estimated simultaneous arrival time at which both the EMS vehicle and the autonomous automotive vehicle will arrive at the rendezvous location.

The availability of the selected EMS service is determined in step 428. If for some reason the selected EMS service cannot accommodate the request for an EMS vehicle, then the EMS service will respond on the same wireless communications channel to notify the autonomous automotive vehicle, whereby another EMS service will be selected in step 412 and the process steps will continue as described above.

When the autonomous automotive vehicle receives acknowledgment from the selected EMS service of availability in step 428, then monitoring of the health status of the passenger will continue in step 432 while the autonomous automotive vehicle travels en route to the selected rendezvous location, and status updates or changes will be communicated in step 424 with the EMS service.

Figure 5:
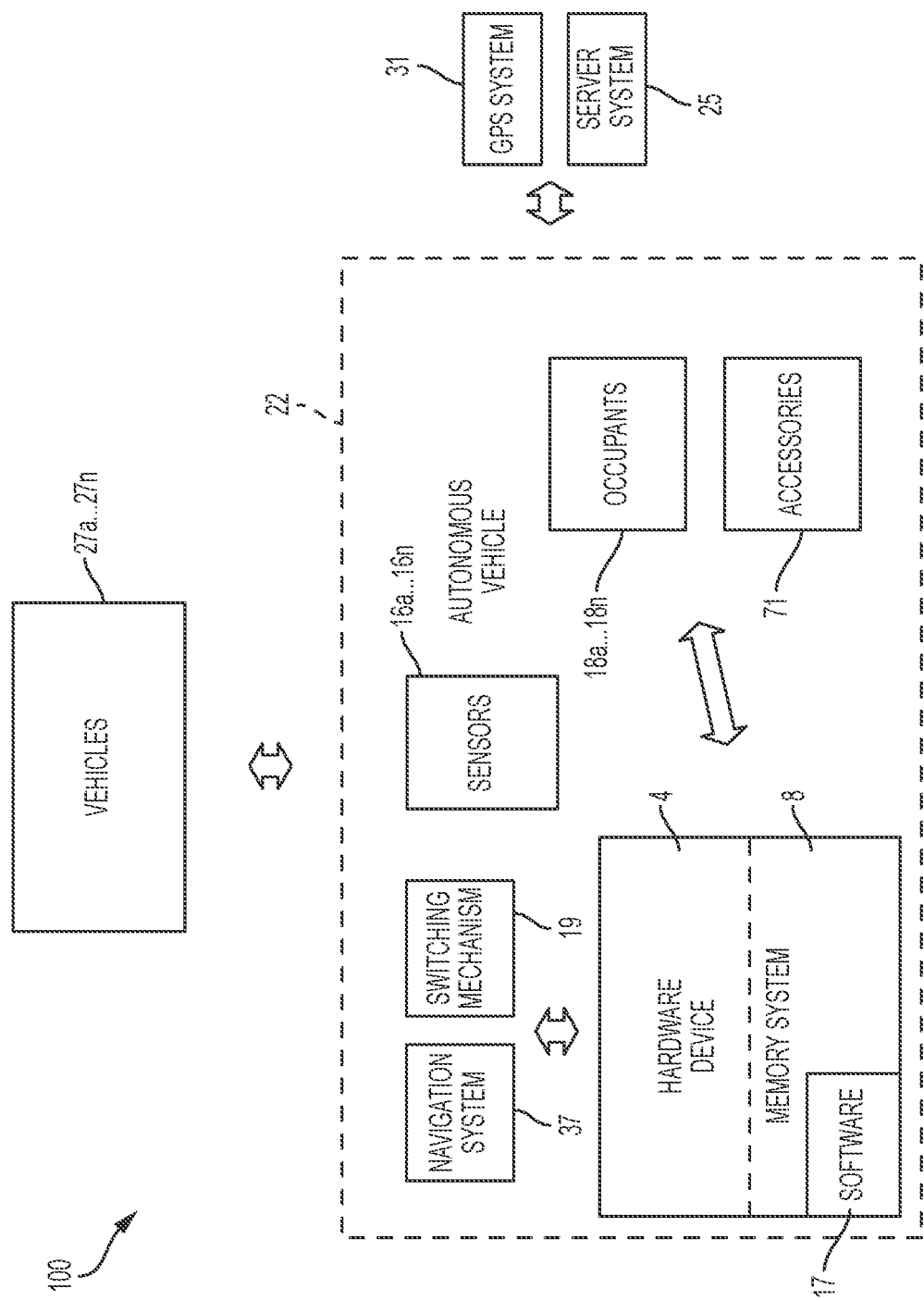
FIG. 5 illustrates a system for improving automotive technology by monitoring vehicle occupant safety and generating associated actions, in accordance with embodiments of the present invention.

FIG. 5 illustrates a system 100 for improving automotive technology by monitoring vehicle occupant safety and generating associated actions, in accordance with embodiments of the present invention. System 100 is enabled to identify an autonomous vehicle occupant having a medical emergency and execute the following actions:

1. Alert predetermined key contacts such as, inter alia, medical assistance personnel, insurance company representatives, family, nearby vehicles, fire stations, first responders, etc.
2. Execute predetermined actions with respect to an autonomous vehicle. Predetermined actions may include, inter alia, disabling the autonomous vehicle, enabling emergency lights of the autonomous vehicle, automatically unlocking doors of the autonomous vehicle, turning a speaker on, auto calling a predetermined phone number, periodically enabling/disabling exterior lights of the autonomous vehicle, periodically enabling/disabling interior lights of the autonomous vehicle, etc.

System 100 of FIG. 1 includes a vehicles 27a . . . 27n, a server system 25, and a global positioning satellite (GPS) (or any type of movement detection system) system 31 communicatively connected (e.g., via a network) to an autonomous vehicle 22. The autonomous vehicle 22 includes a hardware device (e.g., onboard computer 14), a switching (control) mechanism 19, sensors 16a . . . 16n, a navigation system 37, and occupants 18a . . . 18n. Hardware device 14, navigation system 37, and switching mechanism 19 may include any type of hardware controller system(s) including, inter alia, an automobile integrated controller computer, a computer (PC), a laptop computer, a tablet, etc. Hardware device 14 includes a memory system 8. Memory system 8 stores program instructions 17 for enabling a process for monitoring conditions of an occupant of autonomous vehicle 22 and executing vehicular control actions associated with control of autonomous vehicle 22. Hardware device 14, navigation system 37, and switching mechanism 19 may each comprise a specialized hardware device comprising specialized (non-generic) hardware and circuitry (i.e., specialized discrete non-generic analog, digital, and logic-based circuitry) for executing a process described with respect to FIGS. 1-7. The specialized discrete non-generic analog, digital, and logic-based circuitry may include proprietary specially designed components (e.g., a specialized integrated circuit, such as for example an Application Specific Integrated Circuit (ASIC) designed for only implementing a process for improving automotive technology by monitoring conditions of an occupant of autonomous vehicle 22 and executing vehicular control actions associated with control of autonomous vehicle 22). Switching mechanism 19 comprises any type of electrical and/or mechanical control and switching mechanism (for automatically controlling functionality of all accessories 71 in autonomous vehicle 22 as well as all functionality of autonomous vehicle 22) that may include proprietary specially designed electro/mechanical components (e.g., circuitry, switching relay, control motors, etc.). Accessories 71 may comprise any type of functional accessary in vehicle including, inter alia, a radio, air conditioning, power fold down seats, car doors, windows, lights, audio functions, etc. Sensors 16a . . . 16n may include any type of sensors for detecting occupants 18a . . . 18n of vehicle 22. Sensors 16a . . . 16n may include, inter alia, optical sensors, temperature sensors, infrared sensors, speed sensors, GPS sensors, moisture sensors, pressure sensors, motion detector sensors, video cameras, biometric sensors (e.g., heart rate sensors, blood pressure sensors, etc.), etc.

The following process enabled by system 100 of FIG. 1 describes an implementation example for executing vehicular control actions for autonomous vehicle 22:

Autonomous vehicle 22 monitors health conditions (e.g., vital signs) of an occupant (e.g., occupants 18a . . . 18n) via sensors 16a . . . 16n of: autonomous vehicle 22, wearable devices, car seats, video cameras (image recognition), etc. In response, system 100 determines if a health status of the occupant is danger thereby indicating an emergency situation. The determination may be executed by comparing the monitored health conditions with predetermined safe parameters. Additionally, system 100 may receive a direct alert from sensors 16a . . . 16n indicating the emergency situation with respect to the occupant. When an emergency situation is detected, system 100 deploys a plurality of predefined actions for increasing passenger safety and enhancing the occupant's current health conditions. The predefined actions may include, inter alia:

1. Unlocking vehicle doors to enable first responders to quickly access the occupant.
2. Stopping the vehicle to enable first responders to easily reach the occupant.
3. Applying emergency lights to notify additional vehicles of the emergency situation. The emergency light may include standard built it lights or a new set of lights with a distinctive logo/shape to highlight a type of emergency.
4. Enabling a speaker to enable call assistance and communication functionality with the occupant.
5. Periodically enable/disable lights of autonomous vehicle 22 to notify additional vehicles of the emergency situation.
6. Periodically enable/disable lights of autonomous vehicle 22 to stimulate the occupant to keep him/her conscious.

Additionally, system 100 may transmit a plurality of predetermined alerts based on an emergency detected. For example:

1. Transmitting a communication to first responders requesting medical assistance. The communication may include a type of emergency, current occupant health readings, occupant location, vehicle characteristics, etc.
2. Transmitting a communication to predetermined individuals (e.g., family, friends, etc) via email, SMS, real time chat, etc.
3. Transmitting notifications to nearby vehicles. Transmitting notifications may include usage of vehicle to vehicle communication technologies (e.g., V2V). System 100 may transmit a communication to nearby vehicles. This communication may be customized by the occupant to be used with respect to predefined conditions. For example, with respect to a life threatening emergency, the occupant may publish as much information as possible that may guide others to help safe his/her life. Likewise, with respect to a minor emergency, the occupant may not want to transmit any information to nearby vehicles.

Additionally, system 100 may transmit a notification to the occupant's insurance company if required. All notifications may be customized by the occupant to ensure safety and privacy.

Figure 6:
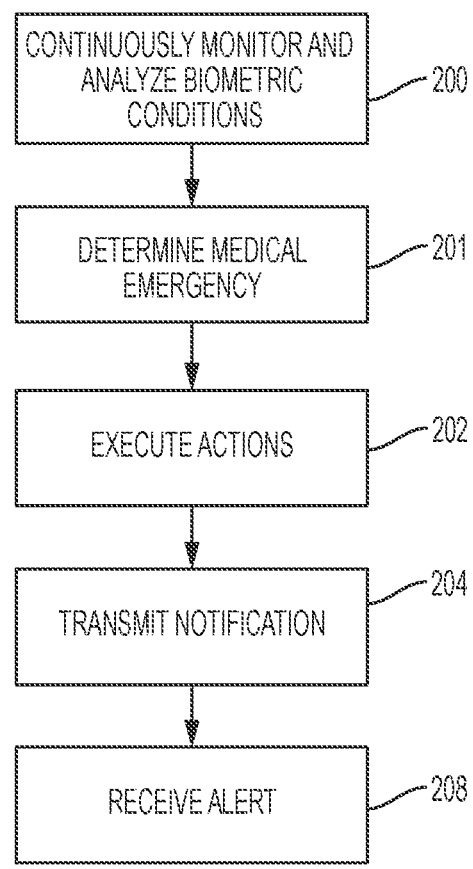
FIG. 6 illustrates a flowchart detailing a process enabled by the system of FIG. 1 for improving automotive technology by monitoring vehicle occupant safety and generating associated actions, in accordance with embodiments of the present invention.

FIG. 6 illustrates a flowchart detailing a process enabled by system 100 of FIG. 1 for improving automotive technology by monitoring vehicle occupant safety and generating associated actions, in accordance with embodiments of the present invention. Each of the steps in the algorithm of FIG. 6 may be enabled and executed in any order by a computer processor executing computer code. In step 200, biometric conditions of an occupant within an autonomous vehicle currently in motion are monitored via a plurality of sensors. The sensors may include, inter alia, sensors within the autonomous vehicle, sensors within a wearable device of the occupant, sensors within a car seat within the autonomous vehicle, etc. The sensors may include thermal imaging sensors, optical sensors, video cameras, altimeters, and IoT proximity sensors, GPS sensors, heartrate monitors, blood pressure monitors, temperature sensors, etc. The biometric conditions are analyzed with respect to predetermined baseline biometric conditions associated with the occupant. In step 201, a medical emergency situation associated with the occupant within the autonomous vehicle currently in motion is detected based on results of step 200. In step 202, predetermined actions associated with resolving the emergency medical situation are executed. The predetermined actions include disabling the autonomous vehicle currently in motion such said motion is terminated. Alternatively, the predetermined actions may include, inter alia, unlocking entry points of the autonomous vehicle, enabling interior and exterior lighting of the vehicle, enabling communications functions of the vehicle, etc. In step 204, a notification indicating the medical emergency situation is transmitted to a predetermined entity. Transmitting the notification may include transmitting a request for an EMS vehicle manned by EMS personnel to be dispatched to a currently detected location of the autonomous vehicle. The request may include currently detected biometric conditions of the occupant and characteristics of the autonomous vehicle. The predetermined entity may include, inter alia, friends or family of the occupant, an insurance company of the occupant, an employer of the occupant, a roadside assistance entity associated with the autonomous vehicle, etc. Transmitting said notification may include transmitting a request to additional vehicles located a predetermined distance from the autonomous vehicle.

In step 208, a direct alert indicating abnormal biometric conditions of the occupant is received from the sensors.

Figure 7:
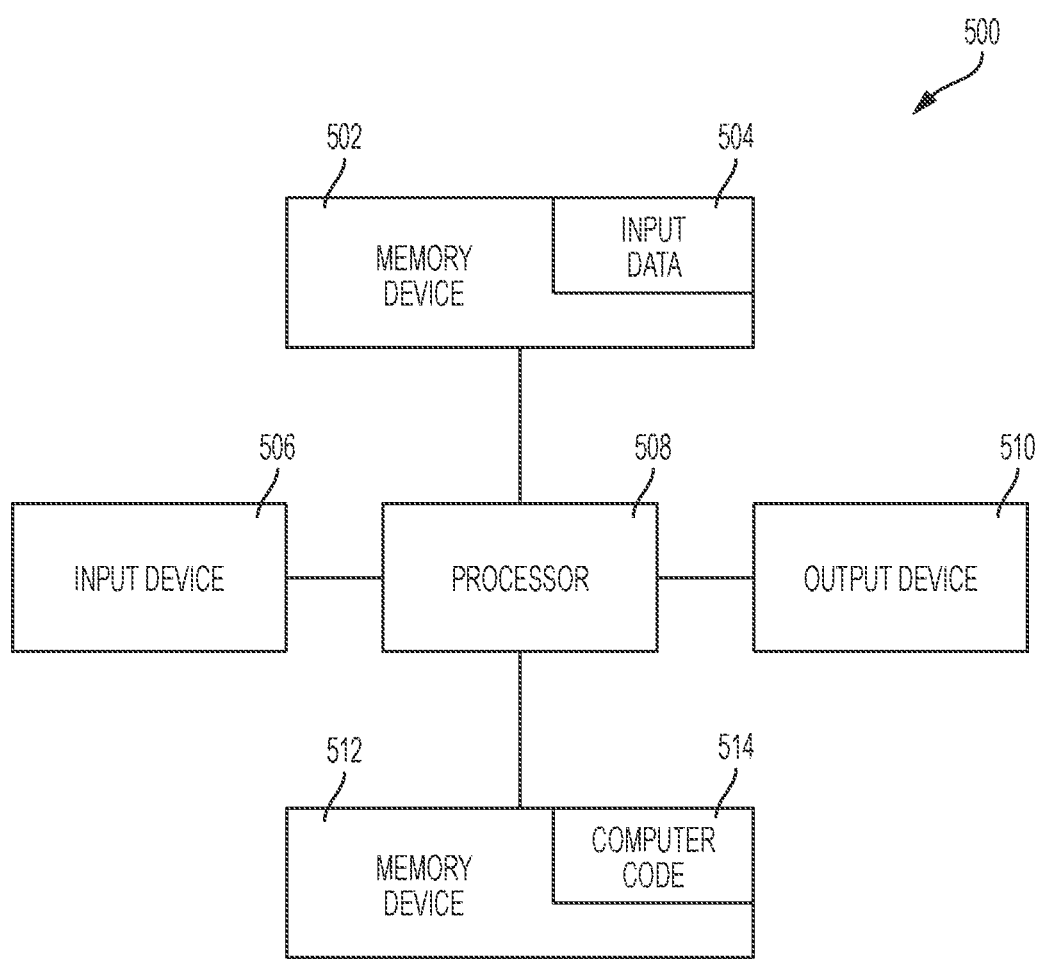
FIG. 7 is a block diagram of a computer system used for implementing the methods of the present invention.

FIG. 7 is a block diagram of a computer system, aka computing device, 500 for improving automotive technology by monitoring vehicle occupant safety and generating associated actions, in accordance with embodiments of the present invention. The computing device 500 includes a processor 508, an input device 506 coupled to the processor 508, an output device 510 coupled to the processor 508, and memory devices 502 and 512 each coupled to the processor 508. The input device 506 may be, inter alia, a keyboard, a mouse, etc. The output device 510 may be, inter alia, a printer, a plotter, a computer screen, a magnetic tape, a removable hard disk, a floppy disk, etc. The memory devices 502 and 512 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 512 includes a computer code 514 which is a computer program that includes computer-executable instructions.

The computer code 514 includes software or program instructions that may implement an algorithm for implementing methods of the present invention. The processor 508 executes the computer code 514. The memory device 502 includes input data 504. The input data 504 includes input required by the computer code 514. The output device 510 displays output from the computer code 514. Either or both memory devices 502 and 512 (or one or more additional memory devices not shown) may be used as a computer usable storage medium (or program storage device) having a computer readable program embodied therein and/or having other data stored therein, wherein the computer readable program includes the computer code 514.

Generally, a computer program product (or, alternatively, an article of manufacture) of the computer system/device 500 may include the computer usable storage medium (or said program storage device). The processor 508 may represent one or more processors. The memory device 502 and/or the memory device 512 may represent one or more computer readable hardware storage devices and/or one or more memories.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block or step of the flowchart illustrations and/or block diagrams, and combinations of blocks/steps in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block or step in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A vehicle occupant safety monitoring method comprising:

monitoring via a plurality of sensors, by a processor of a hardware device within an autonomous vehicle in motion, biometric conditions of an occupant within said autonomous vehicle currently in motion;

analyzing, by said processor, said biometric conditions with respect to predetermined baseline biometric conditions associated with said occupant;

determining, by said processor based on results of said analyzing, a medical emergency situation associated with said occupant within said autonomous vehicle currently in motion;

executing, by said processor, a plurality of predetermined actions associated with resolving said emergency medical situation;

determining, by the processor based on results of said executing, a rendezvous location different than a current location of the autonomous automotive vehicle where the autonomous automotive vehicle and an emergency medical service (EMS) vehicle can meet at an estimated simultaneous arrival time, wherein the determining the rendezvous location step further comprises:

determining the rendezvous location, by the processor, by comparing estimated travel times of the autonomous automotive vehicle and the EMS vehicle to reach a plurality of different safe locations, then selecting the rendezvous location from the plurality of different safe locations which corresponds to a shortest of said estimated travel times, wherein the estimated travel times are each defined as a difference between a current time of the communicated medical emergency situation and estimated simultaneous arrival times at each of the respective plurality of different safe locations; and transmitting, by said processor to a predetermined entity, a notification indicating said a medical emergency situation and results of said executing.

2. The method of claim 1, wherein said sensors comprise integral sensors selected from the group consisting of sensors within said autonomous vehicle, sensors within a wearable device of said occupant, and sensors within a car seat within said autonomous vehicle.

3. The method of claim 1, further comprising:
receiving, by said processor from said plurality of sensors, a direct alert indicating abnormal biometric conditions of said occupant, wherein said determining said medical emergency situation is further based on said direct alert.

4. The method of claim 1, wherein said plurality of predetermined actions comprise disabling said autonomous vehicle currently in motion such said motion is terminated.

5. The method of claim 4, wherein said plurality of predetermined actions further comprise actions selected from the group consisting of unlocking entry points of said autonomous vehicle, enabling interior and exterior lighting of said vehicle, and enabling communications functions of said vehicle.

6. The method of claim 4, wherein said transmitting said notification comprises transmitting a request for an EMS vehicle manned by EMS personnel to be dispatched to a currently detected location of said autonomous vehicle.

7. The method of claim 6, wherein said request comprises currently detected biometric conditions of an occupant and characteristics of said autonomous vehicle.

8. The method of claim 4, wherein said predetermined entity comprises an entity selected from the group consisting of friends or family of said occupant, an insurance company of said occupant, an employer of said occupant, and a roadside assistance entity associated with said autonomous vehicle.

9. The method of claim 4, wherein said transmitting said notification comprises transmitting a request to additional vehicles located a predetermined distance from said autonomous vehicle, and wherein said request comprises currently detected biometric conditions of an occupant and characteristics of said autonomous vehicle.

10. The method of claim 1, wherein said plurality of sensors comprise sensing devices selected from the group consisting of thermal imaging sensors, optical sensors, video cameras, altimeters, and IoT proximity sensors, GPS sensors, heartrate monitors, blood pressure monitors, and temperature sensors.

11. The method of claim 1, further comprising:
providing at least one support service for at least one of creating, integrating, hosting, maintaining, and deploying computer-readable code in the computing system, said computer-readable code being executed by the computer processor to implement: said monitoring, said analyzing, said determining, said executing, and said transmitting.

12. A computer program product, comprising a computer readable hardware storage device storing a computer readable program code, said computer readable program code comprising an algorithm that when executed by a computer processor of a hardware device within an autonomous vehicle in motion implements a vehicle occupant safety monitoring method, said method comprising:

monitoring via a plurality of sensors, by said processor, biometric conditions of an occupant within said autonomous vehicle currently in motion;

analyzing, by said processor, said biometric conditions with respect to predetermined baseline biometric conditions associated with said occupant;

determining, by said processor based on results of said analyzing, a medical emergency situation associated with said occupant within said autonomous vehicle currently in motion;

executing, by said processor, a plurality of predetermined actions associated with resolving said emergency medical situation; determining, by the processor based on results of said executing, a rendezvous location different than a current location of the autonomous automotive vehicle where the autonomous automotive vehicle and an emergency medical service (EMS) vehicle can meet at an estimated simultaneous arrival time, wherein the determining the rendezvous location step further comprises:

determining the rendezvous location, by the processor, by comparing estimated travel times of the autonomous automotive vehicle and the EMS vehicle to reach a plurality of different safe locations, then selecting the rendezvous location from the plurality of different safe locations which corresponds to a shortest of said estimated travel times, wherein the estimated travel times are each defined as a difference between a current time of the communicated medical emergency situation and estimated simultaneous arrival times at each of the respective plurality of different safe locations; and transmitting, by said processor to a predetermined entity, a notification indicating said a medical emergency situation and results of said executing.

13. The computer program product of claim 12, wherein said sensors comprise integral sensors selected from the group consisting of sensors within said autonomous vehicle, sensors within a wearable device of said occupant, and sensors within a car seat within said autonomous vehicle.

14. The computer program product of claim 12, wherein said method further comprises:
receiving, by said processor from said plurality of sensors, a direct alert indicating abnormal biometric conditions of said occupant, wherein said determining said medical emergency situation is further based on said direct alert.

15. The computer program product of claim 12, wherein said plurality of predetermined actions comprise disabling said autonomous vehicle currently in motion such said motion is terminated.

16. The computer program product of claim 15, wherein said plurality of predetermined actions further comprise actions selected from the group consisting of unlocking entry points of said autonomous vehicle, enabling interior and exterior lighting of said vehicle, and enabling communications functions of said vehicle.

17. The computer program product of claim 15, wherein said transmitting said notification comprises transmitting a request for an EMS vehicle manned by EMS personnel to be dispatched to a currently detected location of said autonomous vehicle.

18. The computer program product of claim 17, wherein said request comprises currently detected biometric conditions of an occupant and characteristics of said autonomous vehicle.

19. The computer program product of claim 15, wherein said predetermined entity comprises an entity selected from the group consisting of friends or family of said occupant, an insurance company of said occupant, an employer of said occupant, and a roadside assistance entity associated with said autonomous vehicle.

20. A hardware device, within an autonomous vehicle in motion, comprising a computer processor coupled to a computer-readable memory unit, said memory unit comprising instructions that when executed by the computer processor implements a vehicle occupant safety monitoring method comprising:

monitoring via a plurality of sensors, by said processor, biometric conditions of an occupant within said autonomous vehicle currently in motion;

analyzing, by said processor, said biometric conditions with respect to predetermined baseline biometric conditions associated with said occupant;

determining, by said processor based on results of said analyzing, a medical emergency situation associated with said occupant within said autonomous vehicle currently in motion;

executing, by said processor, a plurality of predetermined actions associated with resolving said emergency medical situation; determining, by the processor based on results of said executing, a rendezvous location different than a current location of the autonomous automotive vehicle where the autonomous automotive vehicle and an emergency medical service (EMS) vehicle can meet at an estimated simultaneous arrival time, wherein the determining the rendezvous location step further comprises:

determining the rendezvous location, by the processor, by comparing estimated travel times of the autonomous automotive vehicle and the EMS vehicle to reach a plurality of different safe locations, then selecting the rendezvous location from the plurality of different safe locations which corresponds to a shortest of said estimated travel times, wherein the estimated travel times are each defined as a difference between a current time of the communicated medical emergency situation and estimated simultaneous arrival times at each of the respective plurality of different safe locations; and transmitting, by said processor to a predetermined entity, a notification indicating said a medical emergency situation and results of said executing.

* * * * *